United States Patent
Joshi (10) Patent No.: US 11,922,796 B2
(45) Date of Patent: Mar. 5, 2024

(54) PREDICTING CRITICAL ALARMS

(71) Applicant: KONINKLIJKE PHILIPS N.V., Eindhoven (NL)

(72) Inventor: Rohan Joshi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 273 days.

(21) Appl. No.: 17/297,910

(22) PCT Filed: Nov. 27, 2019

(86) PCT No.: PCT/EP2019/082739
§ 371 (c)(1),
(2) Date: May 27, 2021

(87) PCT Pub. No.: WO2020/109381
PCT Pub. Date: Jun. 4, 2020

(65) Prior Publication Data
US 2022/0044548 A1     Feb. 10, 2022

(30) Foreign Application Priority Data

Nov. 27, 2018   (EP) .................................... 18208606

(51) Int. Cl.
*G08B 31/00*       (2006.01)
*G16H 20/30*       (2018.01)
*G16H 40/63*       (2018.01)

(52) U.S. Cl.
CPC ............. *G08B 31/00* (2013.01); *G16H 20/30* (2018.01); *G16H 40/63* (2018.01)

(58) Field of Classification Search
CPC ........ G08B 31/00; G08B 21/02; G16H 20/30; G16H 40/63; G06N 20/00; A61B 5/00; A61B 5/7275
See application file for complete search history.

(56) References Cited

U.S. PATENT DOCUMENTS

| 7,225,013 | B2 | 5/2007 | Geva et al. |
| 8,433,260 | B2 | 4/2013 | Kenington et al. |

(Continued)

FOREIGN PATENT DOCUMENTS

| GB | 2560339 A | 9/2018 |
| WO | 2013093692 A2 | 6/2013 |
| WO | 2020011778 A1 | 1/2020 |

OTHER PUBLICATIONS

International Search Report and Written Opinion, International Application No. PCT/EP2019/082739, dated Feb. 4, 2020.

(Continued)

*Primary Examiner* — An T Nguyen (57) ABSTRACT

Embodiments propose methods and system for predicting the occurrence of critical alarms in response to the occurrence of less severe, non-critical alarms. It is proposed to use a machine-learning model trained to discern whether a non-critical alarm will be followed by a critical alarm within a particular time period, e.g. whether the non-critical alarm will develop into a critical alarm. Unlike existing alarm systems which are merely threshold based, this approach uses physiological data from a window of data. This window of data can be expected to carry more information than a simple breach of the threshold.

15 Claims, 4 Drawing Sheets

(56) References Cited

U.S. PATENT DOCUMENTS

| | | |
|---|---|---|
| 9,600,990 B2 | 3/2017 | Hu et al. |
| 2009/0002156 A1 | 1/2009 | Croak et al. |
| 2012/0286955 A1* | 11/2012 | Welch ............... G16H 40/63 340/573.1 |
| 2014/0118138 A1 | 5/2014 | Cobelli et al. |
| 2017/0236071 A1* | 8/2017 | Walker ............ G08B 21/187 706/11 |
| 2022/0044548 A1* | 2/2022 | Joshi ................ G08B 31/00 |

OTHER PUBLICATIONS

Sparacino, G. et al., "Glucose Concentration can be Predicted Ahead in Time From Continuous Glucose Monitoring Sensor Time-Series", IEEE Transactions on Biomedical Engineering, vol. 54, No. 5, May 2007.

Keller JP. Clinical alarm hazards: A top ten health technology safety concern. J Electrocardiol [Internet]. 2012;45 (6):588-91. Available from: http://dx.doi.org/10.1016/j.jelectrocard.2012.08.050.

Chen L, Dubrawski A, Wang D, Fiterau M, Guillame-Bert M, Bose E, et al. Using supervised machine learning to classify real alerts and artifact in online multisignal vital sign monitoring data. Crit Care Med. 2016;44(7):e456-63.

\* cited by examiner

PREDICTING CRITICAL ALARMS

This application is the U.S. National Phase application under 35 U.S.C. § 371 of International Application No. PCT/EP2019/082739, filed on 27 Nov. 2019, which claims the benefit of European Application Serial No. 18208606.6, filed 27 Nov. 2018. These applications are hereby incorporated by reference herein.

FIELD OF THE INVENTION

The invention relates to the field of predicting critical alarms.

BACKGROUND OF THE INVENTION

When monitoring an entity, there is a desire to trigger alarms to indicate deviance from a normal or expected operation of that entity. This can be used to identify when that entity needs attention or is operating in an undesired state.

Such methods of generating an alarm are especially important in a clinical setting to enable clinicians to respond to a deterioration in a subject's or patient's condition. Typically, a subject's physiological parameters (e.g. heart-rate, $SpO_2$ percentage, respiratory rate and so on) undergo continuous monitoring and alarms are generated based on the monitored physiological parameters.

A commonly used method of generating an alarm, from physiological parameters of a subject, is to trigger an alarm when a value of the physiological parameter breaches (e.g. goes above or below) a particular threshold. For example, for an adult male, an alarm may be triggered when their heart-rate falls below 60 beats per minute (bpm) or rises above 100 bpm.

There may be different levels of alarm to indicate different levels of urgency, where more urgent alarms require more immediate clinical attention to prevent subject deterioration. Different levels of alarm may be associated with different thresholds. By way of example, for an adult male, a non-critical alarm may be triggered when their $SpO_2$ percentage (oxygen saturation) falls below 94% and a critical alarm may be triggered when their $SpO_2$ percentage falls below 90%.

Non-critical alarms may alternatively be labelled "yellow alarms" or "advisory alarms". Critical alarms may alternatively be labelled "red alarms" or "urgent alarms".

However, it has been recognized that providing an excess of alarms to a clinician, and especially advisory alarms which may not need immediate attention, can lead to alarm fatigue. Alarm fatigue leads to desensitization of clinicians (or other observers) to alarms, causing the clinicians to ignore or disbelieve the significance of an alarm.

There is therefore a desire to reduce the number of alarms provided to a clinician or other observer of an entity, in an effort to avoid alarm fatigue. There is also a desire to provide alarms as early as possible, in order to minimize a time spent by a subject in a clinically undesirable or dangerous state.

SUMMARY OF THE INVENTION

The invention is defined by the claims.

According to examples in accordance with an aspect of the invention, there is provided a computer-implemented method of predicting the occurrence of a critical alarm for a subject undergoing physiological parameter monitoring. The computer-implemented method comprises: receiving a non-critical alarm signal indicating that the subject has entered a clinically undesirable state at a time of occurrence; and in response to the non-critical alarm signal: obtaining a set of one or more pre-alarm values derived from and/or comprising values of at least one monitored physiological parameter of the subject that fall (or are collected) within a pre-alarm time window of a first predetermined length, wherein the start time of the pre-alarm time window depends upon the time of occurrence of the non-critical alarm signal; and processing, using a machine-learning algorithm, the set of one or more pre-alarm values to generate a predictive indicator indicating a probability that the non-critical alarm signal will be followed, within a post-alarm time window, by a critical alarm signal indicating that the subject has entered a clinically actionable state, wherein the post-alarm time window is of a second predetermined length and begins at the time of occurrence of the non-critical alarm signal.

The invention proposes to predict whether a non-critical alarm (e.g. a "yellow alarm") will develop into or be otherwise followed (within a certain time period) by a critical alarm (i.e. "red alarm"). In response to a non-critical alarm occurring, values of physiological parameters during a pre-alarm time window are processed using a machine-learning algorithm, such as a neural network, to predict whether the non-critical alarm will lead onto a critical alarm.

By accurately predicting the occurrence of a critical alarm following a non-critical alarm, not all non-critical alarms need to be provided to a clinician, thereby reducing the number of alarms that need to be provided to a subject, reducing alarm fatigue. Moreover, a predicted critical alarm can be provided early, thereby minimizing a time spent by a subject in a life-threatening or life-altering state (as a clinician can be alerted before a critical alarm occurs).

A non-critical alarm typically indicates that a subject has entered an undesirable or unhealthy clinical or physiological state (e.g. $SpO_2$ below 94% or malfunctioning equipment), but that urgent clinical attention or medical care is not yet required. A critical alarm typically indicates that the subject requires urgent clinical attention or medical care to avoid entering a life-threatening or life-altering condition (e.g. $SpO_2$ below 90%), e.g. caused by failure of equipment or deterioration of the subject.

In particular embodiments, the non-critical alarm indicates that at least one physiological parameters of the subject has entered a clinically undesirable state at a time of occurrence. In particular, a non-critical alarm may indicate that a value of a monitored physiological parameter has fallen below a threshold value. The threshold value may represent an abnormal or potentially abnormal value for the physiological parameter.

There may be different threshold values associated with different levels of non-critical alarm. For example, a non-critical alarm of a first level may be triggered if a subject's SpO2 falls below 95%, and a non-critical alarm of a second level may be triggered if a subject's SpO2 level falls below 94%. Thus, there may be one or more levels of "non-critical alarms" (e.g. each associated with a particular threshold). In embodiments, e.g. as later described, only some of these alarms (e.g. particular levels of the non-critical alarms) are alerted to a clinician or can be tracked by a clinician.

The non-critical alarm may therefore represent a trigger for determining whether a critical alarm will shortly follow, the trigger being an indication that a subject is in a clinically undesirable state. In preferable embodiments, the non-critical alarm signal only indicates non-critical alarms indicating that a subject has entered a clinically unhealthy state (e.g. according to recognized clinical guidelines).

It has been recognized that not all non-critical alarms will develop into or be otherwise followed by a critical alarm requiring clinical attention. For example, a condition of a subject may self-resolve, an automated system may attend to the non-critical alarm (e.g. automatic increasing of oxygen flow rate) or a non-critical alarm could be unintentionally triggered by noise or (clinically acceptable) natural variations in a subject's condition. The inventor has recognized that a window of physiological parameter data in the vicinity of the non-critical alarm can be used to determine whether the non-critical alarm will develop into a critical alarm. This allows for early prediction of the occurrence of a critical alarm.

Predictive alarming, i.e. before the triggering of a critical alarm, can lead to an earlier response by the clinician, thereby leading to reduced severity and duration of deterioration by a subject. Predictive alarming also means that non-critical alarms need not be brought to the clinician's attention, reducing alarm fatigue.

Another benefit of proposed concepts is that, unlike most machine learning applications in the biomedical context, no expert annotations are required. The absence of expert annotations implies that the concept can be adapted for use in any intensive care or patient monitoring settings by using the routinely monitored physiological parameters (e.g. vital signs, ECG signal) and the corresponding alarm logs of those units. In particular, the approach developed herein may be readily translated to any clinical setting by software updates in existing patient monitoring systems.

The physiological parameters may comprise any of: measurements of (vital) signs, measures from which (vital) signs can be derived or other measurable parameters of the subject. Examples of a physiological parameter include a: PPG (photoplethysmogram) waveform, ECG (electrocardiogram) waveform, chest impedance, heart-rate; heart-rate variability; respiratory rate; $SpO_2$ percentage (oxygen saturation); temperature; blood pressure; blood sugar (glucose) level; subject motion (e.g. derived from an ECG waveform or dedicated motion sensors) and so on.

The predictive indicator may be a binary indicator (indicating whether the machine-learning algorithm believes that a critical alarm will be issued) or a probability (e.g. indicating a probability that the non-critical alarm will develop into a critical alarm). Other suitable predictive indicators, e.g. categorical indicators, will be known to the skilled person.

The start time of the time window may be defined by or be otherwise dependent upon the time of occurrence of the non-critical alarm. For example, the time window may end at the time of occurrence of the non-critical alarm, or may include the time of occurrence of the non-critical alarm.

Preferably, the pre-alarm time window ends at the time of occurrence of the non-critical alarm signal. Thus, the pre-alarm time window is formed of a period immediately preceding the time of occurrence of the non-critical alarm. This would allow the clinician the longest window of opportunity to take pre-emptive clinical action on the predicted critical alarm, thereby reducing the probability that the subject's health will deteriorate.

In some embodiments, one or more values derived from or including values of at least one monitored physiological parameter of the subject that fall (or are collected) within a second post-alarm time window (e.g. smaller in length than the (first) post-alarm time period) may also be used to predict the occurrence of a critical alarm. Thus, values of physiological parameters obtained during a second post-alarm window may be used as additional input for the machine-learning algorithm.

The first predetermined length is preferably greater than the second predetermined length.

There is a desire to minimize the amount of information processed by the machine-learning algorithm (e.g. to improve prediction speed and minimize processing power used), whilst maintaining predictive capabilities. The inventor has recognized that improved accuracy in predicting the occurrence of a critical alarm occurs with a smaller second predetermined length (i.e. when assessing for the occurrence of a critical alarm a short time after the occurrence of a non-critical alarm) and a larger first predetermined length.

Preferably, the length of the first predetermined length is from 1 to 3 minutes, and the length of the second predetermined length is from 1 to 3 minutes. The inventor has recognized that a pre- and post-alarm window of between 1-3 minutes provides the most optimal time period for predicting whether a critical alarm will occur.

The inventor has recognized that, in particular clinical circumstances such as neonatal environments, almost all critical alarms (that have are detectable from a non-critical alarm) are triggered within 3 minutes of the issuance of an associated non-critical alarm. Thus, the benefit of predicting the onset of a critical alarm is lost three minutes after the occurrence of the non-critical alarm in such circumstances.

Of course, it will be appreciated that in other clinical circumstances (e.g. palliative care), there is a larger (average) period between issuance of a non-critical alarm and an associated critical alarm. Thus, the 3 minute upper limit is only of use in some clinical scenarios, such as in neonatal units.

Preferably, the first predetermined length is around 2 minutes (e.g. from 1.8 to 2.2 minutes) and the second predetermined length is around 1 minute (e.g. from 0.8 minutes to 1.2 minutes). The inventor has recognized that such time periods provide a good balance between speed of processing and accuracy.

In embodiments, the computer-implemented method may further comprise, in response to the non-critical alarm, obtaining information about any other alarm for the subject occurring during the pre-alarm time window, wherein the step of processing the obtained values comprises processing at least the obtained values and the information about any other alarm using the machine-learning algorithm to thereby generate the predictive indicator.

It has been recognized that the occurrence and/or type of other (non-critical or critical) alarms within the pre-alarm time window may provide an indicator of the likelihood that a non-critical alarm will develop into a critical alarm. Thus, accuracy of generating the predictive indicator will be increased by also processing information on other alarms within the pre-alarm time window.

The method may further comprise, in response to the non-critical alarm, obtaining metadata of the subject undergoing physiological parameter monitoring, wherein the step of processing the obtained values comprises processing at least the obtained values and the metadata of the subject using the machine-learning algorithm to thereby generate the predictive indicator.

Different subjects will have different likelihoods that a non-critical alarm will develop into a critical alarm. Thus, by using subject metadata to generate the predictive indicator enables population trends to be taken into account, increasing an accuracy and subject-specificity of the predictive indicator.

Subject metadata may include any one or more of the following: age; gestation period or postmenstrual age (especially helpful for neonatal clinical settings); time since admission to the clinical setting or hospital; weight (at admission, birth or current weight); clinical history; clinical diagnosis or diagnoses; treatment plans; presence of ventilatory support; type of ventilation provided (e.g. none, invasive or non-invasive); percentage of supplemental oxygen supplied; type of anesthesia (e.g. none, spinal, epidural, general); fluid resuscitation information (e.g. amount of fluids/blood provided to subject); severity scoring systems (e.g. APACHE, MPM, SAPS or SNAP); medication information; and so on.

The method may further comprise, in response to the non-critical alarm, determining at least one correlation measure indicative of a correlation between two or more values of at least one monitored physiological parameter, wherein the step of obtaining a set of one or more pre-alarm values comprises including the at least one correlation measure in the set of one or more pre-alarm values.

Preferably, the predictive indicator is a binary output indicating a prediction of whether or not the non-critical alarm will be followed by a critical alarm within the post-alarm time window; and the machine-learning algorithm is configured to have a specificity of no less than 0.95.

A high level of specificity (e.g. ≥0.95 or ≥0.98) reduces the number of false positives generated by the method. The inventor has recognized that a high specificity would result in the method being considered reliable by clinicians, and would reduce the likelihood that a clinician will suffer alarm fatigue (e.g. caused by repeated responses to false alarms).

Whilst a high specificity may cause reduced sensitivity of the machine-learning algorithm (e.g. as training data for the machine-learning algorithm cannot always be exhaustive), reduced sensitivity would not affect patient outcome beyond existing methods, as a critical alarm can still be triggered even if the method fails to predict the onset of the critical alarm (based on a corresponding non-critical alarm).

The method may further comprise, in response to the predictive indicator indicating that a likelihood that the non-critical alarm will develop into a critical alarm is at or above a predetermined threshold, generating a first clinician perceptible alert.

A clinician perceptible alert may comprise, for example, audio, visual and/or haptic feedback to a clinician. The first clinician perceptible alert is one that is perceptible by the clinician when they are not actively determining a status of the subject (e.g. a flashing light, a buzzer or siren and/or a vibration). In particular, the first clinician perceptible alert may be one that is typically presented to the clinician in a clinical setting to indicate that a subject has entered a state requiring clinical attention (e.g. to prevent life-changing or life-altering deterioration), typically accompanying critical alarms.

Such embodiments do not exclude the possibility that information on a non-critical alarm will be made available to the clinician (e.g. when actively checking the status of a subject or in a non-perceptible alert), or in the form of a different (second) clinician perceptible alert. In particular a first clinician perceptible alert may be auditory, whereas the different or second clinician perceptible alert may be non-auditory. In other examples, the first clinician perceptible alert may be provided on a (handheld) device to be carried by a clinician (e.g. a pager), whereas the second clinician perceptible alert may not be provided by said device.

In embodiments, the method comprises, in response to the predictive indicator indicating that a likelihood that the non-critical alarm will develop into a critical alarm is below the predetermined threshold, not generating the first clinician perceptible alert.

By only generating the first clinician perceptible alert for a non-critical alarm when it is predicted that the non-critical alarm will develop into or be followed by a critical alarm, a total number of alarms presented to a clinician in the form of a first clinician alerts will be reduced, thereby reducing alarm fatigue and ensuring that only alarms that are predicted to require urgent clinical attention (e.g. critical alarms or predicted critical alarms) are provided to a subject.

As previously noted, the non-critical alarms may be divided into different levels of non-critical alarms. A first or "lower" level of non-critical alarms may represent an "early warning" state (e.g. a highly conservative indicator of a clinically undesirable state). A second or "higher" level of non-critical alarms may represent an "imminent warning" state (e.g. a less conservative indicator of a clinically undesirable state). Either may act as the "non-critical alarm" of the method. Additional levels may be provided indicating different levels of severity.

In embodiments, no clinician perceptible alert is generated for the first level of non-critical alarms, and a (optionally non-audible) clinician perceptible alert is generated for the second level of non-critical alarms. This reduces the number of alerts provided to a subject, whilst still allowing for a more conservative predictions of a critical alarm to take place.

In further embodiments, a certain level or levels of a non-critical alarm (e.g. lower levels) may be inaccessible by a clinician (i.e. they are not alerted to their existence and/or the clinician may be unable to track or access such non-critical alarms). This helps further reduce alarm fatigue or clinician doubt, whilst still enabling such non-critical alarms to trigger prediction of whether a critical alarm will follow. This provides a good balance of clinical awareness and automatic patient monitoring.

The computer-implemented method may further comprise, in response to a critical alarm, generating the first clinician perceptible alert. Thus, in addition to providing a first clinician perceptible alert when it is predicted that a non-critical alarm will develop into a critical alarm, clinician perceptible alerts may also be provided if a critical alarm is generated. This recognizes that not all critical alarms will be associated with a non-critical alarm (e.g. if there is a sudden deterioration in a subject's condition) or that the proposed method may not correctly predict that a critical alarm will occur.

In particular, an auditory alert may be generated (for a clinician) only in response to a critical alarm (signal) and/or a prediction that a critical alarm signal will occur. Such a procedure would inherently be at least as safe as existing systems since critical alarms that might be missed by the proposed system would still be generated upon the usual breach of the threshold.

An additional advantage of implementing proposed models may be a reduction in the likelihood of clustered critical alarms, as there can be an earlier clinical response to the predicted critical alarm To further reduce a number of alerts provided to a clinician, in some embodiments no further first clinician perceptible alert is generated for the critical alarm if a first clinician perceptible alert has already been provided for an associated non-critical alarm. This further avoids alarm fatigue.

The computer-implemented method optionally further comprises: obtaining metadata of the subject undergoing physiological parameter monitoring; and setting the first predetermined length based on the obtained metadata of the subject.

In embodiments, the computer-implemented method is adapted wherein the non-critical alarm signal indicates that at least one physiological parameter of the subject has entered a clinically undesirable, and the method further comprises, in response to the non-critical alarm: obtaining one or more values for the at least one physiological parameter that triggers the non-critical alarm at a time the non-critical alarm is triggered; modifying the first predetermined length based on the obtained one or more values for the at least one physiological parameter that triggers the non-critical alarm at a time the non-critical alarm is triggered.

According to examples in accordance with another aspect of the invention, there is provided a computer program comprising code means for implementing any described claim when said program is run on a computer.

According to examples in accordance with another aspect of the invention, there is provided a system for predicting the occurrence of a critical alarm for a subject undergoing physiological parameter monitoring. The system comprises: an alarm receiving module adapted to receive a non-critical alarm signal indicating that the subject has entered a clinically undesirable state; and an alarm predicting module adapted to, in response to the non-critical alarm: obtain a set of one or more pre-alarm values derived from and/or comprising values of at least one monitored physiological parameter of the subject that fall (or are collected) within a pre-alarm time window of a first predetermined length, wherein the start time of the pre-alarm time window depends upon the time of occurrence of the non-critical alarm signal and wherein the pre-alarm time window ends before or at the time of occurrence of the non-critical alarm signal; and process, using a machine-learning algorithm, the set of one or more pre-alarm values to generate a predictive indicator indicating a probability that the non-critical alarm signal will be followed, within a post-alarm time window, by a critical alarm signal indicating that the subject has entered a clinically actionable state, wherein the post-alarm time window is of a second predetermined length and begins at the time of occurrence of the non-critical alarm signal.

The system may further comprise a user interface arranged to generate a clinician perceptible alert in response to the predictive indicator indicating that a likelihood that the non-critical alarm will develop into a critical alarm is above a predetermined threshold. The user interface may comprise display, speaker or haptic feedback system.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides concepts for predicting the occurrence of critical alarms in response to the occurrence of less severe, non-critical alarms. It is proposed to use a machine-learning model trained to discern whether a non-critical alarm will be followed by a critical alarm within a particular time period, e.g. whether the non-critical alarm will develop into a critical alarm. Unlike existing alarm systems which are merely threshold based, this approach uses physiological data from a window of physiological data. This window of data can be expected to carry more information than a simple breach of the threshold.

Embodiments are therefore based on the realization that the occurrence of a critical alarm can be predicted based on physiological parameters lying within a window of time defined by a non-critical alarm. Thus, a clinician does not need to be alerted to all non-critical alarms, as not all such alarms will require clinical attention, thereby reducing alarm fatigue.

Illustrative embodiments may be used, for example, in a clinical setting to predict the occurrence of critical alarms and reduce alarm fatigue caused by a clinician being repeatedly alerted to alarms, not all of which require clinical attention.

A "critical alarm", carried by a critical alarm signal, indicates that the subject has entered a clinically actionable state, meaning that clinical intervention is required to prevent the subject entering a life-threatening or life-altering condition. A "critical alarm" could be issued when a parameter of the subject falls below a critical level or if a piece of equipment supporting the subject (such as a ventilator) fails or is about to fail. A "critical alarm" may be alternatively labelled a "red alarm" or "severe alarm".

A "non-critical alarm", carried by a non-critical alarm signal, indicates that the subject has entered a clinically undesirable state, but that clinical intervention is not yet required to prevent the subject entering a life-threatening or life-altering condition. Thus, a non-critical alarm may indicate that the subject (or piece of equipment supporting the subject) is outside of a "normal" state for that subject (or piece of equipment). A "non-critical alarm" may be alternatively labelled a "yellow alarm" or "warning alarm".

Examples of alarms include: low heart rate; high heart rate; arrhythmia; asystole; low breathing rate; high breathing rate; apnea; low SpO2; high SpO2; low temperature; high temperature; low systolic pressure; high systolic pressure; low diastolic pressure; high diastolic pressure; low mean blood pressure; high mean blood pressure; low perfusion; poor pallor (subject color); too little or too much subject movement; out of bed detection; low/high cardiac output; low/high stroke volume; and/or low/high blood flow. Further examples of alarms (equipment-based) include, for a ventilator: high peak inspiratory pressure; disconnection of the ventilator circuit; malfunctioning/occluded endotracheal tube; and low $CO_2$ level. Yet further examples include, for an infusion pump: low flow or presence of air in the line.

Figure 1:
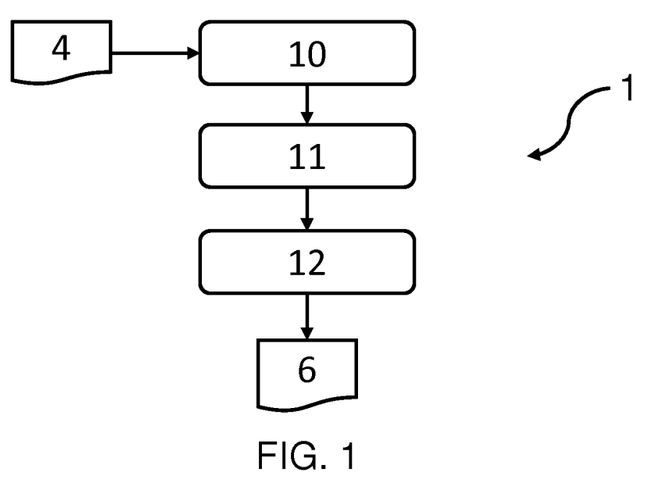
FIG. 1 illustrates a method according to an embodiment.

FIG. 1 is a flowchart illustrating a method 1 according to an embodiment of the invention.

The method comprises a step 10 of receiving a non-critical alarm signal 4 indicating that the subject has entered a clinically undesirable state. This non-critical alarm signal is associated with a "time of occurrence", being the time at which the subject enters the clinically undesirable state.

The method also comprises, in response to the non-critical alarm signal, a step 11 of obtaining a set of one or more pre-alarm values derived from and/or comprising values of at least one monitored physiological parameter of the subject that fall (or are collected) within a pre-alarm time window of a first predetermined length, wherein the start time of the pre-alarm time window depends upon the time of occurrence of the non-critical alarm signal.

Each pre-alarm value comprises either a value of at least one monitored physiological parameter (from the pre-alarm window) or a value derived from (e.g. generated by processing) one or more values of the at least one physiological parameter from the pre-alarm window.

Thus, a value in the set of one or more pre-alarm values may include: a value of the monitored physiological parameter; a processed value of a monitored physiological parameter; a statistical measure of values of the monitored physiological parameter and so on.

A value of at least one monitored physiological parameter may comprise any measure of a subject's condition. Thus, a value of a monitored physiological parameter may comprise any measure responsive to (a change in) the subject's health, status, movement, bodily processes or condition (such as ECG trace, temperature, pulse rate, chest impedance, PPG waveform, breathing rate and so on). Such a value may therefore include raw data from a sensor (such as a raw ECG trace) or processed data from a sensor (such as a determined heart rate from an ECG trace).

Examples of physiological parameters that could be monitored, by measuring values or values that can be processed to measure, include a subject's: heart-rate; heart-rate variability; respiratory rate; $SpO_2$ percentage (oxygen saturation); temperature; blood pressure; blood sugar (glucose) level; subject motion; chest impedance; perfusion index; and so on.

Thus, a pre-alarm value may be a: value of the physiological parameter within the time window; a maximum/minimum value of the physiological parameter within the time window; an average (mean or modal) value of the physiological parameter within the time window; a standard deviation of the value of the physiological parameter within the predetermined time window; a number of times the physiological parameter crosses a predetermined threshold (e.g. the first/second threshold value); a cumulative time that a value of a physiological parameter spends below a threshold value and/or other statistical measures.

Some other envisaged statistical measures, and therefore envisaged pre-alarm values, include: a delta index, a central tendency measure, an approximate entropy, a Lempel-Ziv complexity, a coefficient of correlation, a root mean square and so on.

Thus, step 11 may comprise retrieving values of at least one monitored physiological parameter during the pre-alarm time window, e.g. from a database, and optionally further processing said values, to derive a set of one or more pre-alarm values for use in subsequent step 12.

The method also comprises a step 12 of processing, using a machine-learning algorithm, the set of one or more pre-alarm values to generate a predictive indicator 6 indicating a probability that the non-critical alarm signal will be followed, within a post-alarm time window, by a critical alarm signal. The post-alarm time window is of a second predetermined length, and begins at the time of occurrence of the non-critical alarm signal. A critical alarm signal indicates that (at least one physiological parameter of) the subject has entered a clinically actionable state.

Thus, a machine-learning algorithm is used in step 12 to process values derived from physiological parameters of the subject within a particular time window preceding the non-critical alarm to predict whether the non-critical alarm will shortly, i.e. within a post-alarm time window, be followed by a critical alarm. For example, the machine-learning algorithm may predict whether the non-critical alarm signal will develop into a critical alarm signal.

The probability indicator 6 generated in step 12 may, for example, comprise a predicted probability (e.g. in the range of 0 to 1, or from 0% to 100%) that the non-critical alarm will be followed by a critical alarm within a certain time period. In other examples, the probability indicator will be a binary indicator, indicating whether (e.g. with value '1') or not (e.g. with value '0') the machine-learning algorithm believes that the non-critical alarm will be followed by a critical alarm within a certain time period. Other suitable probability indicators, such as a classification (e.g. indicating "Highly Likely", "Likely", "Unlikely" "Highly Unlikely") will be apparent to the skilled person.

Step 12 may also comprise generating, using the machine-learning algorithm, information about the type of predicted critical alarm, e.g. indicating the cause or label of an event requiring clinical attention indicated by the predicted critical alarm (e.g. dangerously low heart rate, desaturation and so on).

In some embodiments, steps 11 and 12 are only performed in response to the non-critical alarm being provided for a predetermined period of time (e.g. no less than 5 s or no less than 10 s). This prevents potentially unnecessary determination of whether a critical alarm will follow a non-critical alarm (e.g. if a potential issue raised by a non-critical alarm resolves itself), thereby saving processing power.

Figure 2:
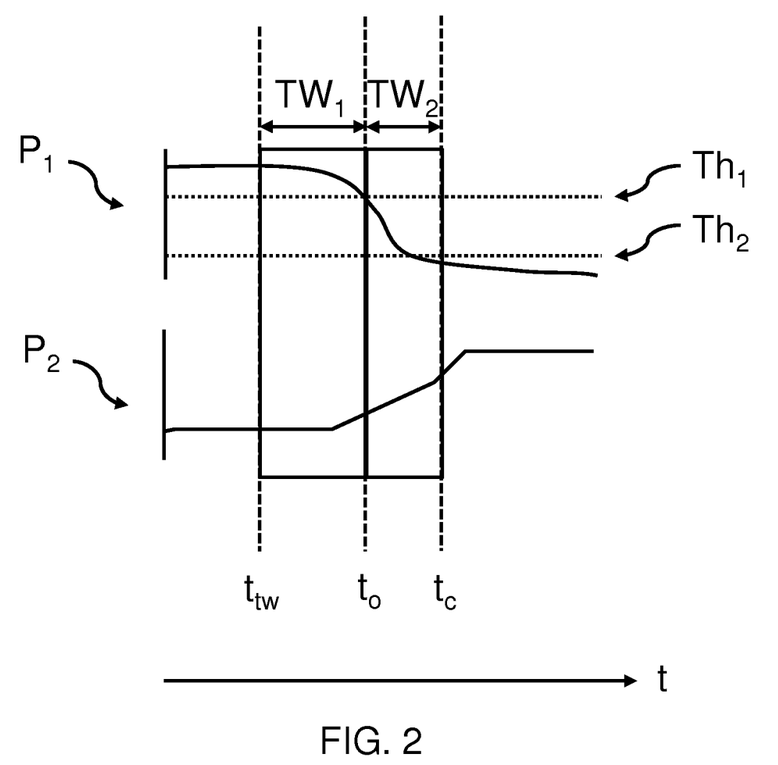
FIG. 2 illustrates timing diagrams for example alarms and time windows.

FIG. 2 illustrates example timings for the non-critical alarm and the pre-alarm and post-alarm time windows, according to an embodiment of the invention.

In particular, FIG. 2 illustrate two example graphs $P_1$, $P_2$ of exemplary physiological parameters over time t. A first graph $P_1$ may represent a subject's $SpO_2$ (oxygen saturation) percentage over time t. A second graph $P_2$ may represent a subject's breathing rate over time t.

A non-critical alarm may be triggered (at a time $t_o$) when a value for a physiological parameter of the subject crosses or reaches a threshold value, which indicates that the subject has entered or will enter a clinically undesirable state. A critical alarm may be triggered (at a time $t_c$) when a value for a physiological parameter of the subject crosses or reaches a different, threshold value, which indicates that the subject will enter a clinically dangerous state without clinical intervention.

In the illustrated example, the subject's $SpO_2$ level is associated with a first threshold value $Th_1$ (e.g. 94%), wherein a non-critical alarm is triggered, at time $t_o$, if the subject's $SpO_2$ level falls below the first threshold value. Furthermore, the subject's $SpO_2$ level is also associated with a second threshold value $Th_2$ (e.g. 90%), where a critical alarm is triggered, at time $t_c$, if the subject's $SpO_2$ level falls below the second threshold value.

Although not illustrated, other physiological parameters (e.g. breathing rate $P_2$) of the subject may be associated with similar threshold values. Threshold values may be a threshold value where if the value of the physiological parameter falls below that threshold (i.e. a "lower-bound" threshold), then an alarm is issued, or a threshold wherein if the value of the physiological parameters rises above that threshold (i.e. an "upper-bound" threshold), then an alarm is issued.

In the scenario illustrated in FIG. 2, the value of the subject's $SpO_2$ level falls below the first threshold value $Th_1$ at a time $t_o$. Thus, a non-critical alarm is generated/issued at a time $t_o$, i.e. the "time of occurrence of a non-critical alarm signal".

In response to the non-critical alarm (signal), a set of one or more values, derived from and/or including values of physiological parameters falling within a pre-alarm time window $TW_1$, are processed by a machine-learning algorithm to predict whether the non-critical alarm will be followed by a critical alarm (within a post-alarm time window $TW_2$ after the time of occurrence $t_o$ of the non-critical alarm). The set of values may be derived from and/or include the value(s) of any monitored physiological parameter, including the physiological parameter that triggered the non-critical alarm.

For example, in the illustrated scenario, values derived from the $SpO_2$ level $P_1$ and the breathing rate $P_2$ can be used/processed to form the set of one or more values used to predict whether the non-critical alarm will be followed by a critical alarm. However, values derived from other physiological parameters may also be included.

The length of the pre-alarm time window $TW_1$ is predetermined. However, the start time $t_{pw}$ of the time window is based upon or depends upon the time of occurrence $t_o$ of the non-critical alarm. That is, the time of occurrence $t_o$ of the non-critical alarm defines or delineates the time at which the time window begins. For example, the start time $t_w$ of the time window may be a certain, predetermined number of minutes before the time of occurrence $t_o$ of the non-critical alarm.

Thus, the pre-alarm time window $TW_1$ corresponds to values of physiological parameters that have already been monitored/recorded.

In preferred examples, and as illustrated in FIG. 2, the pre-alarm time window $TW_1$ ends at the time of occurrence $t_o$. Thus, the start time $t_{pw}$ of the pre-alarm time window may begin the first predetermined length (of time) before the time of occurrence $t_o$. However, in other examples, the pre-alarm time window $TW_1$ ends before the time of occurrence $t_o$.

As illustrated, the length of the pre-alarm time window $TW_1$ is preferably greater than the length of the post-alarm time window $TW_2$. Machine-learning algorithms trained on such restrictions have demonstrated particularly accurate prediction of critical alarms whilst minimizing an amount of processing power required.

A set of one of more values derived from or including the values of the physiological parameters $P_1$, $P_2$ falling within the pre-alarm time window are processed, by a machine-learning algorithm, to generate the predictive indicator.

As previously explained, values derived from a variety of different physiological parameters can be processed to predict the occurrence of a critical alarm.

In preferable further embodiments, other information about the subject, such as metadata, and/or alarms can be used to predict the occurrence of the critical alarm.

In some embodiments, one or more values derived from or including values of at least one monitored physiological parameter of the subject that fall (or are collected) within a second post-alarm time window (e.g. smaller in length than the (first) post-alarm time period) may also be used to predict the occurrence of a critical alarm. Thus, values of physiological parameters obtained during a second post-alarm window may be used as additional input for the machine-learning algorithm.

Figure 3:
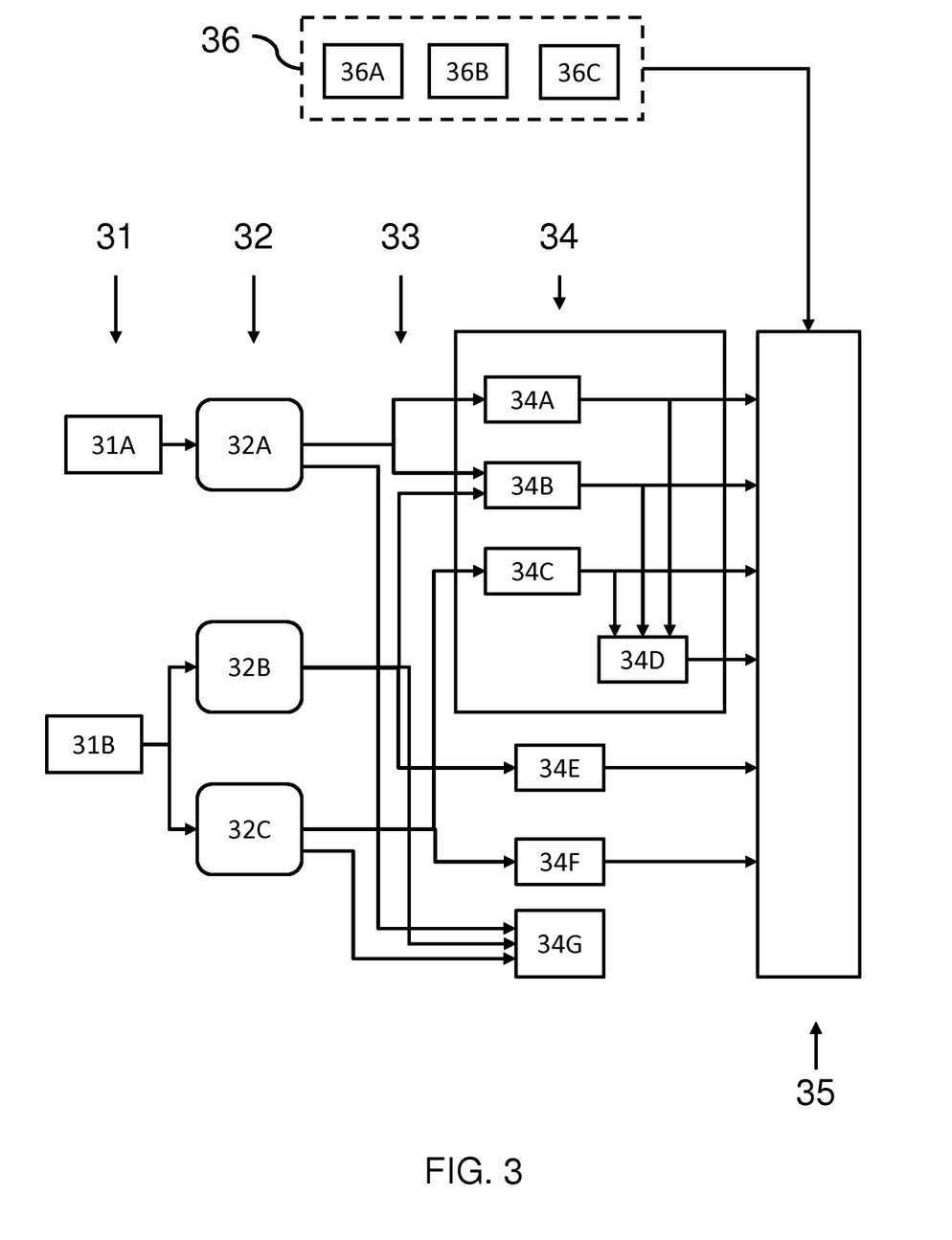
FIG. 3 illustrates a system for deriving values of physiological parameters.

FIG. 3 schematically illustrates how values of the physiological parameters can be obtained and how pre-alarm values can be obtained from said values of the physiological parameters.

FIG. 3 illustrates sensors 31 for detecting physiological parameters of a subject. Here, the sensors comprise a pulse oximeter 31A and ECG (electrocardiogram) electrodes 31B.

FIG. 3 also illustrates (physiological parameter) data 32 obtained from the sensors 31. The data 32 here comprises a photoplethysmogram (PPG) waveform 32A, obtained from the pulse oximeter 31A. The data 32 also comprises an ECG waveform 32B and chest impedance measurements 32C, both obtained from the ECG electrodes 31B. Each physiological parameter data 32 is time-variant.

The data 32 can be processed, e.g. in a step 33, to obtain values of physiological parameters. Each value is associated with a particular time (e.g. a timestamp), and it can therefore be determined whether a value falls inside or outside of a defined time window. Thus, each value of a physiological parameter may be a sample of a physiological parameter of the subject.

In the illustrated example, the PPG waveform 32A can be processed to derive values for the oxygen saturation $SpO_2$ 34A, the pulse/heart-rate 34B and/or estimate a motion 34G of the subject. The ECG waveform 32B can be processed to derive the pulse/heart-rate 34B of the subject, a heart-rate variability 34E of the subject and/or estimate a motion 34G of the subject. The chest impedance measurements 32C can be processed to derive the breathing rate 34C, the respiratory instability 34F and/or estimate a motion 34G of the subject.

One or more of the values 34 may be further processed to derive further values (which are therefore ultimately also derived from the physiological parameter data 32). For example, a correlation value 34D may be derived from different physiological parameter values. For example, a correlation value 34D may indicate a correlation between the oxygen saturation 34A, pulse/heart-rate 34B and/or breathing rate 34C values. Correlation values thereby indicate a measure of correlation between at least two different values 34.

Thus, a set of one or more values 34 comprising one or more values of the physiological parameters and/or one or more values derived by processing one or more values of the physiological parameters is obtained. It will be apparent that the set of one or more values corresponds to values of the physiological parameter that fall (or are collected) within a pre-alarm window.

The set of values 34, derived from the physiological parameter data 32, is processed (e.g. by a processing system 35) to generate a predictive indicator indicating a probability that a non-critical alarm will be followed by a critical alarm, within a certain time period.

In particular, a system 35 performs a step of processing, using a machine-learning algorithm, a set of one or more pre-alarm values 34 derived from values of at least one physiological parameter of the subject to thereby generate a predictive indicator indicating a probability that a non-critical alarm signal will be followed by a critical alarm signal.

Not all of the values 34 need to be used during the processing of the set of one or more pre-alarm values. Rather, in embodiments, a subset of all available values are selected and processed using the machine-learning algorithm. The selection of the subset of available values may depend upon the machine-learning algorithm or patient metadata.

In particular examples, the machine-learning algorithm may be trained or configured to select certain ones of the available values. In other embodiments, patient metadata may be obtained and used to select which of the values 34 are generated (e.g. to gather only the information necessary for a machine-learning algorithm for the subject having that metadata). This improves an efficiency of the overall method.

For example, in a neonatal environment, $SpO_2$ holds the most prognostic potential (primarily because desaturation is the most prevalent red alarm), and so values associated therewith may be included in the subset of values processed to generate the predictive indicator. For other patient populations, the values of most prognostic potential may be different. In particular, it is considered likely that the data most closely associated with the most prevalent alarm for that patient population would be most useful.

As previously noted, in some further embodiments, additional data 36 may also be processed alongside the values 34 to generate the predictive indicator. In other words, a machine-learning algorithm may receive, as input, a set of values 34 and additional data 36 and output the predictive indicator.

The additional data 36 may include: information 36A about the non-critical alarm in response to which the processing is performed; information 36B about any other alarm for the subject occurring during the time window of the predetermined length; and/or metadata 36C of the subject. Using such additional data 36 allows more accurate and bespoke computation of the predictive indicator.

Information 36A about the non-critical alarm may comprise, for example, a label or category associated with the non-critical alarm, a time of occurrence $t_o$ of the non-critical alarm and so on.

Information 36B about any other alarm for the subject may include, for example, a label/category associated with any other alarm occurring during the time window, a time of occurrence of the any other alarms, a number of other alarms occurring during the time window, a number of non-critical alarms occurring during the time window, a number of critical alarm occurring during the time window; a frequency of other alarms occurring during the time window and so on.

Metadata 36C of the subject may include any of or more of the following: age; gestation period (especially helpful for neonatal clinical settings); time since admission to the clinical setting or hospital; weight (at admission, birth or current weight); clinical history; clinical diagnosis or diagnoses; treatment plans and so on.

It has previously been described how there is envisaged a pre-alarm time window and a post-alarm time window. The pre-alarm time window defines which data is provided as input for the machine-learning algorithm. The post-alarm time window defines the period of time for which the machine-learning algorithm attempts to predict whether a critical alarm will occur therein.

The lengths of the time windows affect the accuracy and complexity (and therefore speed) of the machine-learning algorithm. It is therefore desirable to pick appropriate lengths for these time windows.

Preferably, the first predetermined length (the length of the pre-alarm time window) is less than 3 minutes and/or greater than 1 minute. The period of between 1-3 minutes has been identified as providing a good compromise between accuracy and computational complexity, especially for a neonatal environment.

Preferably, the second predetermined length (the length of the post-alarm time window) is less than 3 minutes and/or greater than 1 minute. In particular examples, the second predetermined length is around 1 minute in length (e.g. ±10%). It has been identified that a large majority of critical alarms occur within 1 minute of a non-critical alarm, and computational complexity can therefore be reduced by limiting the length of the post-alarm time window to no more than 1 minute.

As previously explained, different machine-learning algorithms may be used in different environments and/or different patients. Different machine-learning algorithms may use different features (e.g. values derived from physiological data) and/or different first/second predetermined lengths during the prediction process.

To take account of this, in embodiments, the first and/or second predetermined length may depend upon patient metadata.

In some embodiments, the first and/or second predetermined length may be modified based on values of the physiological data (e.g. a heart rate value). In particular, the first predetermined length may modified based on a value of physiological data at a time of occurrence of the non-critical alarm, or based on values of the physiological data that triggered the alarm.

It has previously been described how embodiments utilize a machine-learning algorithm to process (at least) a set of one or more pre-alarm values derived from values of at least one physiological parameter of the subject to thereby generate a predictive indicator indicating a probability that the non-critical alarm signal will be followed by a critical alarm signal.

The machine-learning algorithm may further receive other information, such as metadata or alarm information, which is also processed during generation of the predictive indicator.

The set of one or more pre-alarm values and the other information may be collectively referred to as "input data" or "a set of one or more features". The set of one or more features comprises at least the set of one or more pre-alarm values derived from values of at least one physiological parameter.

Thus, a machine-learning algorithm receives, as input, a set of one or more features and provides, as output, the predictive indicator. The machine-learning algorithm is executed in response to a non-critical alarm signal.

Suitable machine-learning algorithms for being employed in the present invention will be readily apparent to the skilled person. Examples of suitable machine-learning algorithms include decision tree algorithms and artificial neural networks. Other machine-learning algorithms such as logistic regression, support vector machines or Naïve Bayesian model may also be used and perform well. The decision tree is particularly well suited for this application because it permits reclusive partitioning of the feature space.

A decision tree algorithm will be known to the skilled person. A decision tree algorithm is formed from one or more decision nodes, beginning with a root node. Each node (starting with the root node) makes a decision based on input data, and based on an outcome of the decision, directs a next decision or provides an output of the decision tree algorithm.

Methods of training or generating a decision tree algorithm to a training dataset are well known. In examples, a training dataset is provided, formed of training input data entries and corresponding training output data entries. Known methods of generating the decision tree algorithm include the classification and regression tree (CART) algorithm and the Iterative Dichotomiser 3 (ID3) algorithm. Generally, such methods comprise a top-down approach of iteratively identifying possible splits in the training input data (relative to the training output data), quantifying an effectiveness of a possible split (e.g. using a gini index or information gain), and formulating the most effective split into a decision node. In this way, a decision tree can be built up. Decision tree algorithms can be further improved using a boosting algorithm, such as the eXtreme gradient boosting (XGB) algorithm or random forests.

Decision trees are advantageous because, by default, they are able to handle missing data and do not require pre-processing of the data, enhancing the possibility of near real-time performance in clinical settings.

Artificial neural networks or, simply, neural networks, will also be familiar to those skilled in the art. In brief, a neural network is a type of machine-learning model that can be used to process input data to produce output data, such as predicting the probability of a certain scenario occurring based on the input data.

The structure of a neural network is inspired by the human brain. Neural networks are comprised of layers, each layer comprising a plurality of neurons. Each neuron comprises a mathematical operation. In the process of processing input data, the mathematical operation of each neuron is performed on the input data to produce a numerical output, and the outputs of each layer in the neural network are fed into the next layer sequentially. The final layer provides the output.

Methods of training a neural network are well known. Typically, a training set of data is provided, formed of training input data and corresponding training output data. The training input data is processed by the neural network to produce example output data. The example output data is compared to the training output data to determine an accuracy of the neural network (e.g. by using a loss function). The neural network, and in particular the mathematical operations of the neurons, are modified based on the determined accuracy in an effort to improve the accuracy of the neural network (e.g. minimize the loss function). Known methods of modifying the neural network include gradient descent, backpropagation algorithms and so on.

Preferably, the machine-learning algorithm is designed to provide a binary output, indicating whether (e.g. with output '1') it believes the non-critical alarm will be followed by a critical alarm within the post-alarm window or whether (e.g. with output '0') it does not believe that the non-critical alarm will be followed by a critical alarm within the post-alarm window.

Binary (or other classification) output machine-learning algorithms can be trained to target sensitivity or specificity. Sensitivity is a relative measure (e.g. from 0 to 1) of a true positive rate. Specificity is a measure of a false negative rate (i.e. the inverse of the false positive rate).

The inventor has recognized a particular desire to prioritize or target specificity over sensitivity. A high specificity (e.g. $\geq 0.95$ or $\geq 0.98$) would ensure that the model is deemed reliable by clinicians, and thereby reduce alarm fatigue (as clinicians will readily believe that a prediction of a critical alarm is accurate, and act accordingly).

Moreover, even if a high specificity is provided at the expense of a low sensitivity, it has been recognized that critical alarms will still, nonetheless, be issued, albeit at a later point in time even if the machine-learning algorithm does not correctly predict that a critical alarm will follow. Thus, the proposed alarm prediction system would inherently be at least as safe as current systems since critical alarms that might be missed by the machine-learning algorithm would still be generated upon the usual breach of the threshold.

It will be appreciated that it would be beneficial to use different machine-learning algorithms, first predetermined lengths and/or second predetermined lengths for use in different environments. Thus, a different machine-learning algorithm or first/second predetermined length may be used based on information about the environment or clinical setting, information about the subject (e.g. subject metadata).

For example, an algorithm developed for use in a neonatal unit will not perform as well when employed in an adult intensive care unit. Thus, different machine-learning algorithms may be trained using different training data for use in different types of clinical settings (e.g. a neonatal unit v an adult intensive care unit). Alternatively, a generic algorithm (e.g. originally developed for a neonatal unit) could be further trained or tweaked based on training data for a different type of unit (e.g. training data for an adult unit), e.g. once the generic algorithm has already been deployed.

Moreover, even within the same type of clinical setting, different clinical settings (e.g. a first neonatal unit v. a second neonatal unit) may differ in their characteristics, such as using a different thresholds for generating a non-critical or critical alarm, so that an accuracy of a same algorithm may differ between different clinical settings of the same type. Therefore, it would be preferable for an algorithm designed for a particular type of environment to be further trained for a specific clinical setting. This could be performed once the machine-learning algorithm has already been deployed in that environment. For example, an algorithm may be allowed to learn the patterns of alarms from real-world data and regularly update itself (e.g. for a decision tree algorithm, generate a new set of trees) so that it becomes specific to the environment in which is it deployed.

It is also recognized that even within the same clinical setting, thresholds and available sensor data and/or sensor types can also change (over time). Therefore, even within the same clinical setting, it would be preferable for the algorithm to be allowed to update itself regularly (e.g. by using monitored physiological data and alarm data), so it adapts to new data patterns. In this manner, the algorithm can continuously adapt to changes in technology and operation specifications.

In yet further examples, an algorithm can also be allowed to adapt and personalize by learning from data of individual subject. For example, each subject may be associated with their own historical physiological parameter data and alarm data, so that an algorithm can be tuned based on the subject's own historical parameter data. Thus, a generic algorithm may be continually trained (or trained upon subject admittance)

Any one or more of the above approaches can be used to adapt a machine-learning algorithm to a new type of clinical setting, a new clinical setting, to changes in the clinical setting or to different patients.

Figure 4:
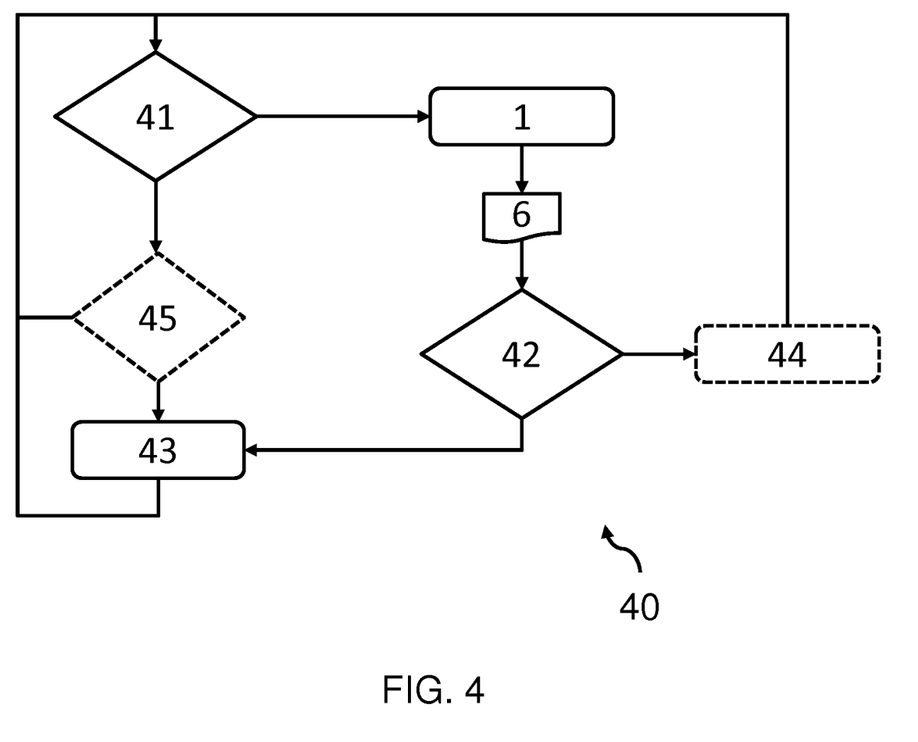
FIG. 4 is a flow chart illustrating a method according to another embodiment.

FIG. 4 illustrates a method 40 according to an embodiment of the invention.

The method 40 comprises a step 41 of determining whether a non-critical alarm has been issued.

In response to step 41 determining that a non-critical alarm has been issued, the method moves to step 1 of predicting the occurrence of a critical alarm for a subject undergoing physiological parameter monitoring. Step 1 may be carried out by performing any previously described method. Step 1 provides, as output, a predictive indicator 6.

Following step 1, the method 40 comprises performing a step 42 of determining whether the predictive indicator 6 indicates that a likelihood that the non-critical alarm will develop into a critical alarm is above a predetermined threshold. The precise implementation of step 42 depends upon the format of the predictive indicator 6.

For example, where the predictive indicator is a binary indicator (where 1 (or 0) means a critical alarm predicted and 0 (or 1) means no critical alarm is predicted), step 42 would comprise determining whether the predictive indicator has value 1 (or 0) (likelihood above predetermined threshold) or value 0 (or 1) (likelihood not above predetermined threshold.

In another example, where the predictive indicator is a probability ranging from 0 to 1, step 42 may comprise determining whether the probability is above a predetermined threshold, e.g. 0.5, 0.6 or 0.7.

In response to step 42 determining that the predictive indicator 6 indicates that a likelihood that the non-critical alarm will develop into a critical alarm is above a predetermined threshold, the method moves to step 43 of generating a first clinician perceptible alert. After issuing the first clinician perceptible alert in step 43, the method may return to step 41.

A clinician perceptible alert may comprise, for example, audio, visual and/or haptic feedback to a clinician. The first clinician perceptible alert is one that is perceptible by the clinician when they are not actively determining a status of the subject (e.g. a flashing light, a buzzer or siren and/or a vibration). In particular, the first clinician perceptible alert may be one that is typically presented to the clinician in a clinical setting to indicate that a subject has entered a state requiring clinical attention (e.g. to prevent life-changing or life-altering deterioration), typically accompanying critical alarms.

In response to step 42 determining that the predictive indicator 6 does not indicate that a likelihood that the non-critical alarm will develop into a critical alarm is above a predetermined threshold, then the method may return back to step 41.

In some embodiments, instead of returning back to step 41, in response to a negative determination in step 42, the method may perform a step 45 of generating a second clinician perceptible alert. The second clinician perceptible alert should be distinguished from the first clinician perceptible alert (e.g. a different sound, color or vibration pattern/intensity). This means that a clinician can still be alerted to the occurrence of a non-critical alarm, whilst being able to distinguish from a predicted critical alarm, and thereby reduces alarm fatigue.

However, in preferable embodiments, no clinician perceptible alerts are generated if step 42 determining that the predictive indicator 6 does not indicate that a likelihood that the non-critical alarm will develop into a critical alarm is above a predetermined threshold. This significantly reduces alarm fatigue.

In some embodiments, in response to step 41 determining that no non-critical alarm being issued, the method may move to a step 44 of determining whether a critical alarm has been issued.

In response to step 44 determining that a critical alarm has been issued, the method moves to step 43 of issuing the first clinician perceptible alert. Thus, the alert issued when a critical alarm is issued may be the same as well it is predicted that a critical alarm will be issued.

This enables machine-learning algorithms with a high level of specificity (e.g. $\geq 0.95$ or $\geq 0.98$) to be used, as any missed predictions of critical alarms will nonetheless be drawn to the clinician's attention in response to the issuance of the critical alarm. Thus, alarm fatigue can be reduced by only issuing the first clinician perceptible alert in response to a (highly confident) prediction of a critical alarm and/or the critical alarm itself.

In preferable embodiments, no first clinician alert is issued in step 43 in response to a critical alarm signal if that critical alarm signal has already been predicted (and an appropriate first clinician alert already generated) in step 1.

In response to step 44 determining that no critical alarm has been issued, the method may return to step 41 (i.e. and not issue any alarm).

Thus, methods 40 is an iterative process that responds to any issued alarms or signals containing the alarm.

In some embodiments, the machine-learning algorithm is designed to indicate a type of critical alarm that is predicted to occur within the post-alarm time period. In such embodiments, step 43 may comprise (when triggered by step 42) providing an indication of the predicted type of critical alarm. Of course, step 43 may also comprise (when triggered by step 44) providing an indication of the type of critical alarm triggered.

A full description of examples for preparing a suitable machine-learning algorithm, and selecting the predetermined lengths, for use in the present invention is hereafter provided for the sake of improved understanding. In the described example, the machine-learning algorithm is adapted for use in a neonatal unit.

Physiological data and alarm data from a number of preterm infants (being subjects of a neonatal unit) is obtained for generating the machine-learning algorithm. Optionally, additional information about the preterm infants (e.g. metadata) is also obtained.

Physiological data may be obtained be performing non-invasive monitoring of the subjects. For example, values of vital cardiorespiratory signs, to monitor each subject's heart-rate, breathing rate, and SpO2, can be obtained from electrocardiogram measurements (from a 3-lead ECG), impedance pneumography measurements and pulse oximetry measurements respectively. These values can be retrospectively acquired from a subject monitoring system (such as the Philips IntelliVue MX800) at an appropriate resolution (e.g. 1 Hz) via a data warehouse. The raw ECG waveforms (e.g. at 250 Hz) could also be extracted and used to analyze the heart-rate variability (HRV).

Alarm data, e.g. comprising a logs of alarms for each preterm infant, identifying at least timings of all non-critical ("yellow") and critical ("red") alarms can also be extracted. Each alarm could be associated with a relevant category or label. For example, "desaturation" and "bradycardia" are categories of critical alarms and "SpO2-low" and "SpO2-high" are categories of non-critical alarm.

As previously explained, a machine learning algorithm can be trained based on example input data and corresponding example output data. To generate the example input data and example output data, an entry for the example input data, and a respective entry for the example output data, can be generated for each non-critical alarm in the alarm data.

In particular, for each non-critical alarm identified in the alarm data, physiological data from a pre-alarm time window of a first predetermined length is obtained (for an entry of the example input data) and an indication of whether that non-critical alarm was followed by a critical alarm within a post-alarm time window of a second predetermined length is also obtained (for a corresponding entry of the example output data).

The obtained/extracted physiological data contributes to the entry for the example input data. The obtained/extracted indication contributes to the corresponding entry for the example output data.

More specifically, to obtain an entry of the example input data, the physiological data for an entry may be further processed to obtain a set of one or more pre-alarm values derived from values of the physiological parameters within a pre-alarm window. Thus, an entry of example input data comprises at least a set of values formed from or derived from values of at least one monitored physiological parameter of a subject falling within the pre-alarm window.

In some embodiments, each entry of example input data further comprises subject metadata (of the subject associated with the physiological values) and/or alarm information about alarms occurring within the pre-alarm time window and/or the non-critical alarm associated with the entry of example input data.

In this way, an entry of example input data comprises a number of features (e.g. values derived from physiological parameters, values of physiological parameters, patient metadata and/or alarm information).

An entry of the example output data comprises at least an indication of whether the non-critical alarm (associated with that entry) was followed by a critical alarm within a post-alarm time window. The entry of the example output data may also comprise information on the type of the critical alarm.

The machine-learning algorithm is then trained using the example input data and the example output data. In particular, the machine-learning algorithm is trained to learn the relationship between example input data and the example output data. A training example is hereafter described.

The example input data and the example output data can be randomly split into training (e.g. 80%) and test (e.g. 20%) sets, stratified by the proportion of NonCritical-to-Critical (NCtC) alarms and NonCritical-to-No-Critical (NCtC) alarms in the original dataset. The training data is used to train the machine-learning algorithm. The test data is used to test the suitability of the machine-learning algorithm.

By way of explanation, all non-critical alarms that were followed by at least one critical alarm within the post-alarm window can be termed NonCritical-to-Critical (NCtC) alarms and constitute the case cohort while those non-critical alarms that do not lead to a critical alarm (NCtnC) constitute the control cohort.

Table I illustrates, according to some real-life sample data, the total number of non-critical alarms that were followed by critical alarms within different second predetermined lengths ($PD_2$), as well as the total number of non-critical alarms that were not followed by a critical alarm within the different second predetermined lengths $PD_2$. Whilst the data from Table I represents real-life samples in a neonatal unit, it is considered illustrative of general trends in this environment. Table I helps illustrate the odds of making a correct prediction without exploiting any information from the features.

TABLE I

| $PD_2$ (min) | No. of NCtC alarms | No. of NCtnC alarms |
| --- | --- | --- |
| 3 | 47,255 | 149,007 |
| 2 | 40,869 | 155,387 |
| 1 | 31,901 | 164,352 |

Using the training data, a machine-learning algorithm (such as a decision tree) can be generated. For example, a CART (classification and regression tree) algorithm can be used to generate the decision tree based on the gini impurity index. The algorithm may restrict a maximum depth of the tree for the purposes of efficiency, e.g. to no more than 6 levels.

An eXtreme gradient boosting (XGB) algorithm (implemented via the XGBoost library) can be employed to boost the prediction performance. Gradient boosting is an ensemble method that incrementally creates new trees to predict the residual errors in predictions up to the previous level, and then combines all trees to make the final improved prediction. It is called gradient boosting since it uses a gradient descent algorithm to minimize the cost function upon adding new trees to the ensemble. The first tree in this ensemble is equivalent to the unboosted decision tree. Consequent trees are tuned to predict the error in the classification of the ensemble up to that point.

Preferably, the machine-learning algorithm is trained to have a high specificity (e.g. ≥0.95 or ≥0.98), for reasons previously set out. Training to a specificity is possible using a CART algorithm, as well as using many other training methods.

In this way, a machine-learning algorithm can be trained to predict, based on at least a set of values derived from values of monitored physiological parameters within at least a pre-alarm time window, whether a given non-critical alarm will be followed by a critical alarm within a post-alarm time window.

In embodiments, the machine-learning algorithm can also be trained to predict, if issued, the type of critical alarm that is issued during the post-alarm time window. This requires each entry of example output data to include information on the type of alarm (if present) generated during the post-alarm time window.

As previously set out, the features used as input to the machine-learning algorithm include values derived from and/or comprising values of physiological parameters of the subject falling within a pre-alarm window. The output is a predictive indicator of whether a critical alarm will occur in a post-alarm window. Indeed, it is a concept of this invention is to use physiological parameters within a pre-alarm time window in the vicinity of a non-critical alarm to predict whether the non-critical will be followed or will develop into a critical alarm within a post-alarm time window.

It is therefore important to choose an appropriate length for the time windows when generating the machine-learning algorithm, as well as appropriate values derived from physiological parameters. There is therefore a need to define/select the length of the pre-alarm time window and the post-alarm window, as different time windows may require different machine-learning algorithm.

The length of the post-alarm time window should be selected to account for any reasonable delay in the production of the critical alarm from the non-critical alarm.

In a neonatal environment, due to rapid changes in infant condition, it is observed that 3 minutes is a suitable, and realistic, maximum delay between a non-critical alarm and an associated critical alarm being issued (i.e. critical alarms more than 3 minutes after a non-critical alarm cannot necessarily be associated with that non-critical alarm).

In more detail, an appropriate length for the post-alarm time window could be obtained by observing the typical transition times, being a time delay between a non-critical alarm and a following critical alarms, e.g. by selecting an average transition time, or by selecting a transition time below which a predetermined percentage of transitions occur. Transition times can be obtained from the alarm data.

Figure 5:
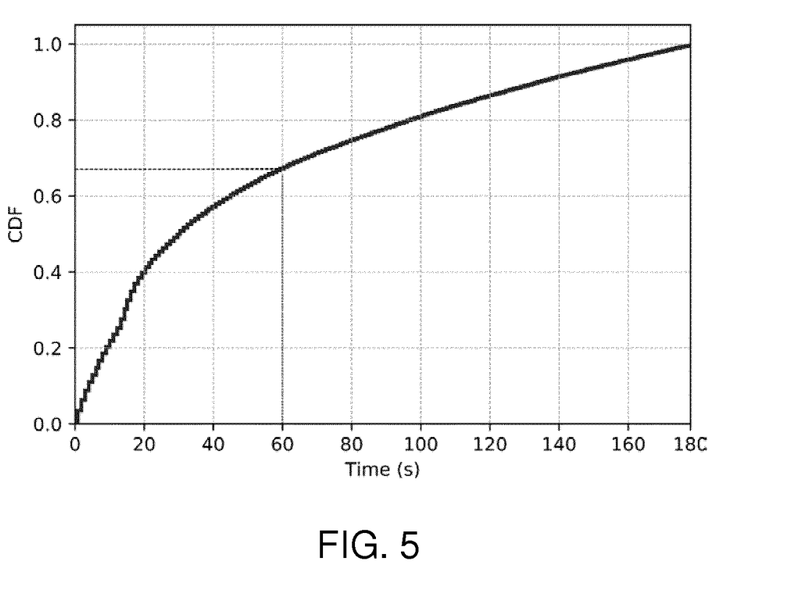
FIG. 5 illustrates characteristics of a relationship between a length of time after a non-critical alarm and the issuance of a critical alarm.

FIG. 5 illustrates an example cumulative density function (CDF) over a period of time, censored at 3 minutes, of transition times for real-life sample data in a neonatal environment (i.e. derived from alarm data). Based on the cumulative density function of times using this real-life sample data, it has been identified that, when critical alarms occur within 3 minutes, 65% of them occur within 60 s of a preceding non-critical alarm. Thus, 1 minute would appear to be an appropriate length for the post-alarm time window (as this would predict the majority of the alarms).

In another example, to select appropriate lengths for the pre-alarm or post-alarm time windows, different instances of machine-learning algorithms could be trained for different lengths of the time windows, and the best or best compromise algorithm could be selected.

For example, based on clinical insights (e.g. as shown in the cumulative density function of FIG. 5), both the first and second predetermined lengths (of the pre-alarm and post-alarm time windows respectively) could be initially chosen to range between 1-3 minutes, and different instances of machine-learning algorithms developed for a number of different combinations within this range.

For example, machine-learning algorithms could be developed with the first predetermined length held at 3 minutes while the second predetermined length is changed between 3, 2 and 1 minute. Machine-learning algorithms could also be developed with the first predetermined length being changed from 2 to 1 minutes respectively while the second predetermined window was held constant at 1 minute. Thus, 5 different instances of machine-learning algorithms could be produced based on different combinations of first and second predetermined lengths. Other suitable selections for predetermined lengths for instances of the machine-learning algorithm could be made, where appropriate.

Each algorithm can then be trained using the training set of data.

After training, the performance of the machine-learning algorithm can be quantified by processing the test set of data using the trained machine-learning algorithm and determining a performance metric of the machine-learning algorithm, such as AUROC or sensitivity.

The AUROC represents a measure of accuracy of the machine-learning algorithm. Other suitable loss functions for measuring accuracy will be apparent to the skilled person, and can replace the AUROC.

In an example, a machine-learning algorithm can be selected based on or using at least the determined performance metric of each machine learning algorithm (with the appropriate lengths of the pre-alarm and post-alarm time windows automatically selected).

In other example, a subset of the (best-performing) algorithms may be further trained, e.g. using a boost algorithm. For example, for the best-performing machine-learning algorithm (e.g. best 3), as measured by the performance metric using the test set, the eXtreme gradient boosting (XGB) algorithm (implemented via the XGBoost library) could be employed to boost the prediction performance.

Each boosted machine algorithms can then be re-assessed to determine the boosted performance metric of each boosted machine-learning algorithm. The boosted performance metrics can then be used to select which boosted machine-learning algorithm to use in an embodiment of the method.

Of course, it is not necessary to boost any machine-learning algorithm, and this step may be omitted. Rather the selection of the machine-learning algorithm may be performed based on the initially trained machine-learning algorithm (as previously described). In yet another embodiment, every instance of the machine-learning algorithm (e.g. and not just the best-performing) is boosted and subsequently assessed.

Selection of a machine-learning algorithm (from the trained set of machine learning algorithms) may therefore depend upon at least a performance metric of the machine-learning algorithm. In some embodiments, selection is further based on a complexity measurement of each machine-learning algorithm.

Complexity of the machine algorithm can be assessed by determining an average length of time or processing power required to compute an output for each instance of input test data. The complexity measurement may also be used to select which machine-learning algorithm to use in an embodiment of the invention.

For example, a compromise choice between complexity and performance may be made to select an appropriate machine-learning algorithm. Selection may be performed, for each machine-learning algorithm, summing the complexity and performance measurement (either of which may be suitably weighted and/or scaled) to produce a summed measurement, and selecting the machine-learning algorithm having the highest summed measurement.

Looking at general trends, it has been observed that performance, as measured by AUROC and sensitivity, improved upon shortening the second predetermined length (for the post-alarm time window) whereas changing the pre-alarm window (for the pre-alarm time window) had a limited effect on performance.

In particular, machine-learning algorithms have been identified as being particularly advantageous when the length of the post-alarm time window is less than the length of the pre-alarm time window, and preferably wherein the length of the post-alarm time window is around 1 minute (±10%).

Based on real-life sample data for a neonatal environment, processed according to the above method, it has been identified that a pre-alarm time window having a length of 2 minutes and a post-alarm time window having a length of 1 minute provides a suitable compromise between complexity of the machine-learning algorithm and the performance of the machine-learning algorithm.

It has also been recognized that not all available or conceivable features (e.g. available in each entry of the example input data) need to be used by a machine-learning algorithm to provide accurate prediction of output information (here predicting an alarm). Rather, only a subset of possible features need to be used. Using only a subset reduces a complexity of the machine-learning algorithm, thereby speeding up a prediction process.

Thus, different features to be used when predicting the occurrence of critical alarm following a non-critical alarm could be identified. Each feature represents, for example, a (derived) value of the monitored physiological parameters of the subject(s), subject metadata and/or alarm information.

Each feature may be part of a 'feature family', representing a particular type of physiological parameter, metadata or type of alarm information. For example, features of a 'heart-rate family' may comprise an average heart-rate within the pre-alarm time window; a maximum heart-rate within the pre-alarm time window; a minimum heart-rate within the pre-alarm time window and so on. Features of a 'non-critical alarm information family' may comprise an identifier of the physiological parameter associated with the alarm, an indicator of the type of alarm (e.g. high or low) and so on.

Example feature families may include: (i) infant metadata; (ii) information on the category of the non-critical alarm generated; (iii) information on other alarms in the pre-alarm time window (e.g. a number of other alarms); (iv) values representing the heartrate in the pre-alarm time window; (v) values representing the breathing rate in the pre-alarm time window; (vi) values representing the $SpO_2$ level in the pre-alarm time window the SpO2; (vii) correlation between the heart-rate, the breathing rate and the SpO2 level and (viii) the heart-rate variability.

It is possible to characterize the standalone predictive potential of features from each category as well as the predictive potential in combination with one another to identify the most important physiological data for alarm prediction.

In particular, in embodiments, only a selection of the possible available features and/or values are selected for acting as inputs to the machine-learning algorithm. Thus, some available features (namely, those that contribute the least to accurately predicting the occurrence of a critical alarm) may be dropped.

One method of selecting features is hereafter described, where the machine-learning algorithm is formed of a decision tree. In particular, a feature selection process can be used on some or all of the available features to reduce the dimensionality of feature matrix by determining the smallest set of features with the most prognostic potential.

To determine such a smallest set, for each feature family, different instances of machine-learning algorithms can be trained on all possible combinations of 1 feature, 2 features up to n features within that family at a time until the best performing "n" feature combination is within a certain threshold of the best performing "n−1" feature combination (e.g. where an AUROC is less than 0.001). The "n−1" feature combination is selected, and the next feature family processed in the same way.

This approach can be considered as an exhaustive feature selection process with a specific stopping criterion (e.g. AUROC increase <0.001). For instance, for the heart-rate feature family (e.g. formed from 13 different features), if the best performing combination of 6 features had a mean AUROC (from CV) that was higher than the best performing combination of 5 features by 0.001 or less, the 5 best-performing features would be inducted into the combined feature-pool.

This procedure of exhaustive feature selection at the feature-family level, can be carried out for each feature family to constitute the final feature-pool. In this way, a machine-learning algorithm can be trained to use only a subset of available features, namely using only a subset of features from each feature-family.

Whilst the above-described approach uses a brute-force methodology for feature selection, at the feature-family level, other feature selection methods to identify a suitable combination of all features (e.g. not at the feature-family level) will also work reasonably well.

In embodiments, some of the 'feature families' are excluded from the feature selection process (i.e. are always included as features), such as those features that do not relate to values of physiological parameters (e.g. alarm information or metadata).

The above-described feature selection process may be integrated into the proposed method for selecting a machine-learning algorithm with an appropriate pre-alarm and post-alarm window.

For example, the above-described feature selection process may be performed on each instance of the machine learning algorithm (where each instance is associated with a different length of pre-alarm and/or post alarm time window). This ensures that the most efficient machine-learning algorithm is selected.

The skilled person would be readily capable of developing a system for carrying out a previously described method. Thus, each step of the flow chart may represent a different action performed by a system, and may be performed by different modules of the system.

Figure 6:
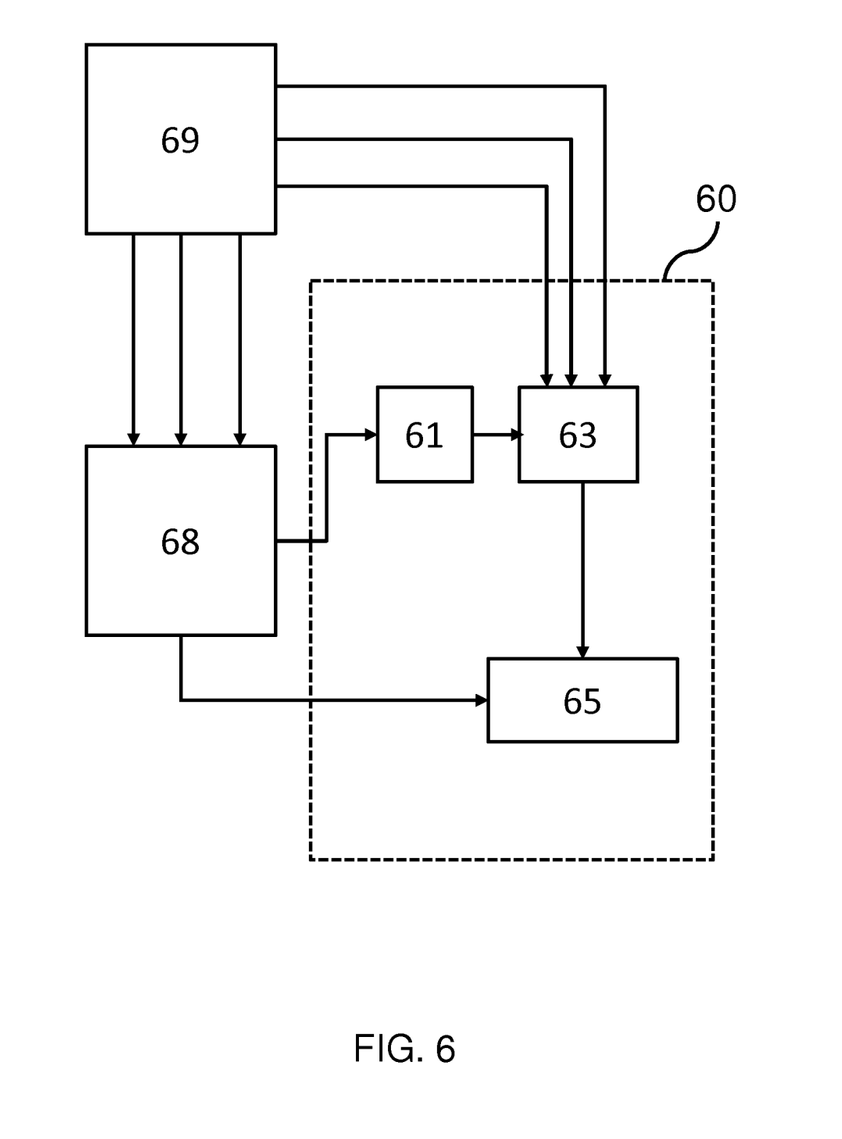
FIG. 6 is a block diagram illustrating a system according to an embodiment.

Nonetheless, for the sake of completeness, FIG. 6 illustrates a system 60 according to an embodiment of the invention. The system 60 comprises an alarm receiving module 61 and an alarm predicting module 63.

The alarm receiving module 61 is adapted to receive a non-critical alarm signal indicating that (at least one physiological parameter of) the subject has entered a clinically undesirable state.

The alarm predicting module 63 is adapted to, in response to the non-critical alarm, obtain a set of one or more pre-alarm values derived from and/or comprising values of at least one monitored physiological parameter of the subject that fall (or are collected) within a pre-alarm time window of a first predetermined length, wherein the start time of the pre-alarm time window depends upon the time of occurrence of the non-critical alarm signal.

The alarm predicting module 63 is also adapted to process, using a machine-learning algorithm, the set of one or more pre-alarm values to generate a predictive indicator indicating a probability that the non-critical alarm signal will be followed, within a post-alarm time window, by a critical alarm signal indicating that (at least one physiological parameter of) the subject has entered a clinically actionable state, wherein the post-alarm time window is of a second predetermined length and begins at the time of occurrence of the non-critical alarm signal.

The system 60 may further comprise a user interface 65 arranged to generate a first clinician perceptible alert in response to the predictive indicator indicating that a likelihood that the non-critical alarm will develop into a critical alarm is above a predetermined threshold.

The user interface may comprise, for example, a display, a speaker, a haptic element and so on, so that the first clinician perceptible alert may comprise a visual, audio and/or haptic alert (such as a flashing light, a buzz/siren and/or a vibration).

The alarm receiving module 61 may receive the non-critical alarm signal from an alarm generating device 68. The alarm generating device 68 is adapted to monitor physiological parameters generated by a subject monitor 69, and generate alarm signals when values of the physiological parameter fall below or rise above certain threshold values.

For example, the alarm generating device may generate a non-critical alarm signal if a $SpO_2$ level of a monitored subject falls below a first threshold (e.g. 94%) and generate a critical alarm signal if a $SpO_2$ level of a monitored subject falls below a second, lower threshold (e.g. 90%). In further examples, the alarm generating device may generate a second non-critical alarm signal if an $SpO_2$ level falls below a third threshold (e.g. 95%), to thereby implement a multi-level non-critical alarm concept.

The alarm generating device may be adapted to communicate with the user interface 65, so that the user interface can respond to at least critical alarms, e.g. by issuing a first clinician perceptible alert.

Thus, non-critical alarms may trigger an operation of the alarm receiving module and critical alarms may trigger the user interface to issue a first clinician perceptible alert.

As discussed above, embodiments make use of a system. The system can be implemented in numerous ways, with software and/or hardware, to perform the various functions required. A processor is one example of a system which employs one or more microprocessors that may be programmed using software (e.g., microcode) to perform the required functions. A system may however be implemented with or without employing a processor, and also may be implemented as a combination of dedicated hardware to perform some functions and a processor (e.g., one or more programmed microprocessors and associated circuitry) to perform other functions.

Examples of system components that may be employed in various embodiments of the present disclosure include, but are not limited to, conventional microprocessors, application specific integrated circuits (ASICs), and field-programmable gate arrays (FPGAs).

In various implementations, a processor or system may be associated with one or more storage media such as volatile and non-volatile computer memory such as RAM, PROM, EPROM, and EEPROM. The storage media may be encoded with one or more programs that, when executed on one or more processors and/or systems, perform the required functions. Various storage media may be fixed within a processor or system or may be transportable, such that the one or more programs stored thereon can be loaded into a processor or system.

It will be understood that disclosed methods are preferably computer-implemented methods. As such, there is also proposed the concept of computer program comprising code means for implementing any described method when said program is run on a computer. Thus, different portions, lines or blocks of code according to an embodiment may be executed by a processor/computer to perform any herein described method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method of predicting the occurrence of a critical alarm for a subject undergoing physiological parameter monitoring, the computer-implemented method comprising:
   receiving a non-critical alarm signal indicating that the subject has entered a clinically undesirable state at a time of occurrence; and
   in response to the non-critical alarm signal:
      obtaining a set of one or more pre-alarm values derived from and/or comprising one or more values of at least one monitored physiological parameter of the subject collected within a pre-alarm time window ($TW_1$) of a first predetermined length, wherein the start time ($t_{pw}$) of the pre-alarm time window depends upon the time of occurrence ($t_o$) of the non-critical alarm signal and wherein the pre-alarm time window ends before or at the time of occurrence of the non-critical alarm signal; and
      processing, using a machine-learning algorithm, the set of one or more pre-alarm values to generate a predictive indicator indicating a probability that the non-critical alarm signal will be followed, within a post-alarm time window ($TW_2$), by a critical alarm signal indicating that the subject has entered a clinically actionable state,
   wherein the post-alarm time window is of a second predetermined length and begins at the time of occurrence of the non-critical alarm signal.

2. The computer-implemented method of claim 1, wherein the pre-alarm time window ($TW_1$) ends at the time of occurrence ($t_o$) of the non-critical alarm signal.

3. The computer-implemented method of claim 1, wherein the first predetermined length is greater than the second predetermined length.

4. The computer-implemented method of claim 1, wherein the first predetermined length is from 1 to 3 minutes, and the second predetermined length is from 1 to 3 minutes.

5. The computer-implemented method of claim 1, further comprising, in response to the non-critical alarm, obtaining information about any other alarm for the subject occurring during the pre-alarm time window,
   wherein the step of processing the obtained values comprises processing at least the obtained set of one or more pre-alarm values and the information about any other alarm using the machine-learning algorithm to thereby generate the predictive indicator.

6. The computer-implemented method of claim 1, further comprising, in response to the non-critical alarm, obtaining metadata of the subject undergoing physiological parameter monitoring,
   wherein the step of processing the obtained values comprises processing at least the obtained set of one or more pre-alarm values and the metadata of the subject using the machine-learning algorithm to thereby generate the predictive indicator.

7. The computer-implemented method of claim 1, further comprising, in response to the non-critical alarm, determining at least one correlation measure indicative of a correlation between two or more values of at least one monitored physiological parameter,
  wherein the step of obtaining a set of one or more pre-alarm values comprises including the at least one correlation measure in the set of one or more pre-alarm values.

8. The computer-implemented method of claim 1, wherein:
  the predictive indicator is a binary output indicating a prediction of whether or not the non-critical alarm will be followed by a critical alarm within the post-alarm time window; and
  the machine-learning algorithm is configured to have a specificity of no less than 0.95.

9. The computer-implemented method of claim 1, further comprising, in response to the predictive indicator indicating that a likelihood that the non-critical alarm will develop into a critical alarm is at or above a predetermined threshold, generating a first clinician perceptible alert.

10. The computer-implemented method of claim 9, further comprising, in response to the predictive indicator indicating that a likelihood that the non-critical alarm will develop into a critical alarm is below a predetermined threshold, not generating the first clinician perceptible alert.

11. The computer-implemented method of any of claim 1, further comprising:
  obtaining metadata of the subject undergoing physiological parameter monitoring; and
  setting the first predetermined length based on the obtained metadata of the subject.

12. The computer-implemented method of claim 1, wherein the non-critical alarm signal indicates that at least one physiological parameter of the subject has entered a clinically undesirable state, the method further comprising, in response to the non-critical alarm:
  obtaining one or more values for the at least one physiological parameter that triggers the non-critical alarm at a time the non-critical alarm is triggered;
  modifying the first predetermined length based on the obtained one or more values for the at least one physiological parameter that triggers the non-critical alarm at a time the non-critical alarm is triggered.

13. A non-transitory computer-readable medium that stores therein a computer program product, which, when executed on a processor, causes the method of claim 1 to be performed.

14. A system for predicting the occurrence of a critical alarm for a subject undergoing physiological parameter monitoring, the system comprising:
  an alarm receiving module adapted to receive a non-critical alarm signal indicating that the subject has entered a clinically undesirable state; and
  an alarm predicting module adapted to, in response to the non-critical alarm:
    obtain a set of one or more pre-alarm values derived from and/or comprising values of at least one monitored physiological parameter of the subject collected within a pre-alarm time window ($TW_1$) of a first predetermined length, wherein the start time ($t_{tw}$) of the pre-alarm time window depends upon the time of occurrence ($t_o$) of the non-critical alarm signal and wherein the pre-alarm time window ends before or at the time of occurrence of the non-critical alarm signal; and
    process, using a machine-learning algorithm, the set of one or more pre-alarm values to generate a predictive indicator indicating a probability that the non-critical alarm signal will be followed, within a post-alarm time window ($TW_2$), by a critical alarm signal indicating that the subject has entered a clinically actionable state,
  wherein the post-alarm time window is of a second predetermined length and begins at the time of occurrence of the non-critical alarm signal.

15. The system of claim 14, further comprising a user interface arranged to generate a clinician perceptible alert in response to the predictive indicator indicating that a likelihood that the non-critical alarm will develop into a critical alarm is above a predetermined threshold.

* * * * *